United States Patent [19]

Kobylinski et al.

[11] 4,116,995
[45] * Sep. 26, 1978

[54] HYDROCARBON SYNTHESIS USING A RARE EARTH PROMOTED METAL SILICATE

[75] Inventors: Thaddeus P. Kobylinski; Harold E. Swift, both of Gibsonia, Pa.

[73] Assignee: Gulf Research & Development Company, Pittsburgh, Pa.

[ * ] Notice: The portion of the term of this patent subsequent to Mar. 30, 1993, has been disclaimed.

[21] Appl. No.: 745,630

[22] Filed: Nov. 29, 1976

[51] Int. Cl.$^2$ ............................................. C07C 27/06
[52] U.S. Cl. ..................... 260/449.6 M; 260/449 M; 260/449.6 R
[58] Field of Search .......................... 260/449 M, 449.6

[56] References Cited

U.S. PATENT DOCUMENTS 3,947,483   3/1976   Kobylinski ........................ 260/449.6

OTHER PUBLICATIONS

Mills, "Catalysis Reviews" 8(2) p. 195 (1973).

*Primary Examiner*—A. Siegel

[57] ABSTRACT

The conversion of carbon monoxide and hydrogen to produce a mixture of low molecular weight hydrocarbons which, on a methane-free basis, contain a predominance of $C_2$-$C_6$ paraffins is achieved using as the catalyst a rare earth metal promoted layered complex metal silicate composition characterized as having repeating units of the structural formula $$[(1-x)Ni^a + xRu^b]_n(OH)_4Si_2O_5 \cdot wH_2O$$

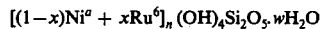

where $x$ is a number from 0 to 1, this number expressing the atomic fraction of the metals nickel and ruthenium; $a$ is the valence of nickel; $b$ is the valence of ruthenium; $n$ is a number equal in value to that defined by the ratio $$6/[a(1-x) + bx]$$

and $w$ is a number ranging from 0 to 4. A rare earth promoted nickel chrysotile is the preferred catalyst.

33 Claims, No Drawings

HYDROCARBON SYNTHESIS USING A RARE EARTH PROMOTED METAL SILICATE

In accordance with 35 USC 120, specific reference is hereby made to the following application, the benefit of the filing date of which is hereby claimed: Ser. No. 613,467 filed Sept. 15, 1975, now abandoned, in the names of Thaddeus P. Kobylinski and Harold E. Swift and assigned to the same assignee as the present application.

This invention relates to the conversion of carbon oxides such as carbon monoxide and carbon dioxide and hydrogen to a mixture of low molecular weight hydrocarbons which, on a methane-free basis contain a predominance of $C_2$-$C_6$ paraffins using an improved metal chrysotile catalyst. In particular, this invention relates to the use of a rare earth metal promoted nickel chrysotile for the conversion of carbon monoxide and hydrogen to low molecular weight hydrocarbons.

BACKGROUND OF THE INVENTION

The reaction of carbon monoxide and hydrogen (so-called synthesis gas) to form methane and higher carbon number hydrocarbons has been described in the prior art. Nowhere, however, is there a description in the prior art of how to control or effect the distribution of the $C_2+$ hydrocarbons in the product so as to peak or maximize the production of $C_2$ to $C_6$ hydrocarbons, i.e. LPG hydrocarbons rather than the higher carbon number gasoline and diesel range type hydrocarbons. A catalyst must be employed, and the prior art catalysts include iron, nickel and ruthenium, among others. U.S. Pat. No. 3,974,483, issued Mar. 30, 1976 in the names of T. P. Kobylinski and H. E. Swift, teaches the use of certain layered complex metal silicates, typified by nickel chrysotile, for the reaction of CO and hydrogen to produce solely methane. It is to be noted that the nickel chrysotile is selective to the formation of methane. Volume IV of "Catalysis" by P. H. Emmett and published by Reinhold Publishing Co., N.Y. (1956) (see pp. 56 et seq.) teaches the use of nickel plus thoria as a catalyst for the production of gasoline range hydrocarbons from synthesis gas. The same reference teaches the use of cobalt plus thoria for the same purpose. It is also well known that nickel alone on kieselguhr produces methane as substantially the sole product by the reaction of synthesis gas in the presence of the nickel catalyst. Pollitzer et al., for example, in U.S. Pat. No. 3,361,535, teach the removal of small amounts of CO from a hydrogen stream by a methanation step embodying the reaction:

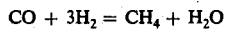

(Col. 4, lines 10-13). Pollitzer et al. teach that various hydrogenation or synthesis catalysts comprising iron, nickel, or more particularly metals of the Iron and Platinum Groups may be used to effect the CO methanation; however, according to Pollitzer et al., a nickel containing catalyst is preferred to obtain the maximum conversion to methane (Col. 4, line 20). Various promoting agents or metallic hydrogenating components are suggested by Pollitzer et al. to be used in combination with nickel or to be incorporated with the support to assist in the methanation step. With regard to the addition of "silica, zirconia, thoria, ceria, beryllia, vanadia, etc." to alumina, Pollitzer et al. teach that "certain" of these "may" have a catalytic or promotional effect but then only in assisting the methanation step. There are no suggestions or teachings in Pollitzer et al. that any hydrocarbons other than methane are intended to be or would be produced using any of their suggested catalytic materials. More importantly, the Pollitzer et al. invention relates to the removal of less than one percent carbon oxide from a stream containing 90% or more hydrogen (Col. 5, lines 45-46). Thus the hydrogen to CO ratio is extremely high, and, as will be shown with the data below, as the hydrogen to CO ratio increases, the amount of $C_2$ plus hydrocarbons dramatically decreases. Even if, for the sake of argument only, the Pollitzer et al. reference was considered as teaching or suggesting the production of higher carbon number products than methane, there is no suggestion regarding (i) the distribution of such hydrocarbon products or (ii) which of the many materials taught as having a "catalytic or promotional" effect would produce predominantly hydrocarbon products having from 2 to 6 carbon atoms per molecule.

U.S. Pat. No. 2,517,035 to Sensel et al. teaches the use of lanthanum oxide in combination with magnesia as a promoter for a cobalt containing catalyst. However, Sensel et al. provide no indication in their specification as to the breakdown of the types of hydrocarbon products which they have obtained. That is, Sensel et al. simply indicate that the product is a $C_3+$ liquid hydrocarbon. Cobalt catalysts are known to produce hydrocarbons in the 4-8 and higher carbon atom range. (H. H. Storch et al., "The Fischer Tropsch and Related Syntheses", John Wiley & Sons, N.Y. (1951), p. 151).) Manganese is also known to be effective as a promoter for nickel catalysts for the production of gasoline range hydrocarbons (see again P. H. Emmett's book referred to above, p. 58). Nickel, on the other hand, per se, is not known as a catalyst to produce gasoline range hydrocarbons, but rather is employed to produce methane alone.

The present invention uses a rare earth promoted nickel chrysotile catalyst not only to accelerate the hydrogenation reaction but also to selectively produce low molecular weight hydrocarbons. By adding rare earths to the nickel chrysotile catalyst, it is possible to obtain significant amounts of $C_2$ to $C_6$ hydrocarbons in addition to methane. Further, there are only very small amounts of $C_7+$ products made.

An improved synthesis reaction is accomplished in accordance with the invention by contacting CO, $CO_2$, or mixtures of these carbon oxides and hydrogen wherein the molar ratio of the hydrogen to carbon oxides is from 1:1 to 4:1 under synthesis conditions including a temperature from 300° to 500° F. (149° to 260° C.) in the presence of a catalyst consisting essentially of a rare earth promoted crystalline layered complex metal silicate characterized as having repeating units having the structural formula:

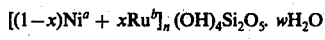

where $x$ is a number from 0 to 1, this number expressing the atomic fraction of the metals mickel and ruthenium; $a$ is the valence of nickel; $b$ is the valence of ruthenium; $n$ is a number equal in value to that defined by the ratio $$6/[a(1-x) + bx]$$

and $w$ is a number ranging from 0 to 4. The hydrocarbon product on a methane-free basis is found to contain at least 60 mole percent of low molecular weight hydrocarbons having from 2 to 6 carbon atoms per molecule.

The improved hydrogenation catalyst for use in the process of this invention is a known layered complex metal silicate wherein the metal is selected from nickel, ruthenium, or mixtures of these metals. These layered complex metal silicates and their methods of preparation are described, for example, in U.S. Pat. No. 3,729,429 to Robson, issued Apr. 24, 1973. The specification of the Robson patent is incorporated herein by reference for the purpose of providing a fuller description of the metal silicates and their method of preparation. It is realized that the materials described by Robson encompass many complex metal silicates while only the nickel and ruthenium or mixed nickel-ruthenium complex metal silicates are claimed in this specification as useful materials to promote the hydrogenation reaction. Robson in his specification describes his metal silicates as useful catalytic agents in hydrocarbon conversion reactions. Illustrative of such reactions are aromatization, isomerization, hydroisomerization, cracking, hydrocracking, polymerization, alkylation, dealkylation, hydrogenation and dehydrogenation, desulfurization, denitrogenation and reforming (see Col. 3, lines 14-18 of the Robson U.S. Pat. No. 3,729,429). Nowhere does Robson teach or indicate that his materials, especially the nickel or ruthenium forms, are useful for the synthesis of low molecular weight hydrocarbons.

More specifically, the catalyst used to promote the desired reaction in accordance with this invention is a rare earth promoted crystalline layered complex metal silicate composition characterized as having repeating units having the structural formula $$[(1-x)Ni^a + xRu^b]_n(OH)_4Si_2O_5 \cdot wH_2O$$

where $x$ is a number from 0 to 1, this number expressing the atomic fraction of the metals nickel and ruthenium; $a$ is the valence of nickel; $b$ is the valence of ruthenium; $n$ is a number equal in value to that defined by the ratio

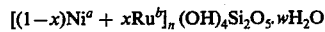

$$6/[a(1-x) + bx]$$

and $w$ is a number ranging from 0 to 4.

The preferred metal silicate is where $x$ in the above formula equals 0. The resulting material is a nickel chrysotile, and naturally occurring nickel chrysotile is known as garnierite.

Thus either naturally occurring nickel chrysotile can be employed to promote the subject reaction, or, more preferably, a synthetically prepared nickel chrysotile can be employed. One suitable method of preparing the catalysts of this invention is, as noted above, by the technique of Robson in U.S. Pat. No. 3,729,429. As noted by Robson at the top of Column 4, $Ni_3(OH)_4Si_2O_5$ (garnierite) is found in nature in the form of tubes. Robson acknowledges that synthetic garnierite has been prepared by prior art workers. The nickel chrysotile used in the working examples later in this specification, however, was prepared in accordance with the techniques of Robson, and thus the Robson technique is the preferred, although not the only, method of preparing the catalyst for use in the subject invention. In general, this process is to initially synthesize a gel be coprecipitation of the metal oxide or hydroxide with hydrous silica gel in an alkaline medium wherein the pH is above 10, preferably about 12 to 14. The composition of the metal hydroxide layer of the crystal is fixed by selecting the concentration of the nickel and ruthenium salts to vary the ratio of nickel to ruthenium as desired. Any water soluble nickel or ruthenium salts can be employed. After the desired gel is produced, it is heated from approximately 200° to 350° C., preferably 250° to 275° C., so that the chrysotile product is crystallized from the synthesis gel with rejection of excess water and soluble salts which are removed by filtration and washing. The complex metal silicates as defined above are generally prepared synthetically in hydrated form and are then converted to a dehydrated form by heating prior to use or in situ operation. Since the dehydration reaction is reversible and since water is produced during the hydrogenation reaction, the exact degree of hydration of the catalyst as the reaction proceeds is not known. Thus $w$ in the above formula is defined as ranging from 0 to 4 to indicate that the degree of hydration of the catalyst may vary.

The nickel, ruthenium, or mixed nickel-ruthenium chrysotiles are dried to remove surface moisture and may or may not be dehydrated in whole or in part by calcination prior to use. The catalyst also, preferably, undergoes a mild prereduction before use. Calcination is not essential, nor is prereduction with a gas such as hydrogen essential, although varying degrees of calcination and/or prereduction may occur. Since the hydrogenation reaction is operated at elevated temperatures and in the presence of reducing gases, dehydration and reduction of the catalyst will occur. Precalcination can suitably occur at temperatures of 300° to 500° C. for 2 to 10 hours. Prereduction using a gas such as $H_2$ at flow rates of 50 to 500 cc/min can also suitably occur at temperatures of 300° to 500° C. for 2 to 10 hours.

The metal silicate, preferably nickel chrysotile, is promoted using rare earth metals or rare earth metal oxides for the conversion of carbon monoxide and hydrogen to low molecular weight hydrocarbons, i.e. hydrocarbons having 1 to 6 carbon atoms. The product consists of a hydrocarbon portion and a non-hydrocarbon portion. The non-hydrocarbon product consists of $H_2O$, $H_2$ and perhaps some unreacted CO or $CO_2$, while, of course, the "hydrocarbon product" consists mostly of paraffins including methane and higher carbon number paraffins. Typically the methane-free hydrocarbon product contains at least 60 mole percent of $C_2$ to $C_6$ paraffins, usually at least 70 mole percent $C_2$ to $C_6$ paraffins, and optimally at least 90 mole percent $C_2$ to $C_6$ paraffins. By "promotion" is meant the activity of the metal silicate (as measured by conversion) increases together with an increase in selectivity to the production of $C_2$ to $C_6$ hydrocarbons. The rare earth metal or rare earth metal oxide is dispersed uniformly in the nickel chrysotile by any suitable means, for example, by physical admixture; or, more usually and preferably, by deposition from a solution, preferably aqueous, of a suitable salt, such as a rare earth metal nitrate. Such rare earths are difficult to reduce; they are usually present in the oxide form. Rare earth metals including the oxide form and mixtures of these metals which can be used include metals having the following atomic numbers: 21, 39, 57 to 72, and 90. Mixtures of the rare earths are preferred. A promoting amount of rare earth metal oxide is employed and this is usually from 0.5 to 25 weight percent, preferably 1.5 to 5 weight percent of the total catalyst.

The charge stock for the synthesis reaction comprises hydrogen and at least one carbon oxide selected from the group consisting of CO and $CO_2$ wherein the molar ratio of hydrogen to combined carbon oxides is from 1:1 to 4:1. Preferably the hydrogen to combined carbon oxides molar ratio is from about 1:1 to 2.5:1 more preferably from 1:1 to 2.2:1; and most preferably from 1:1 to 2:1. As will be shown below, as the $H_2$ to CO ratio increases, the amount of $C_2+$ hydrocarbons decreases. Since the process of this invention is directed to the production of LPG type paraffins, the lower hydrogen to combined carbon oxide ratios are preferred.

Ideally the synthesis reaction proceeds in accordance with Equation 1 when CO is the reactive carbon oxide employed.

Equation 1

$$(2n + 1)H_2 + nCO \rightleftarrows C_nH_{2n+2} + nH_2O$$

For instance, when $n$ equals one,

Equation 1(a)

$$3 H_2 + CO \rightleftarrows CH_4 + H_2O$$

or when $n$ equals three,

Equation 1(b)

$$7H_2 + 3CO \rightleftarrows C_3H_8 + 3H_2O$$

Referring to Equations 1, 1(a) and 1(b), stoichiometry indicates that the minimum hydrogen to CO mole ratio is 2:1. Hydrogen to CO ratios as low as 1:1 can be used, as noted previously, but reduced reaction efficiency results. Higher hydrogen to CO ratios, above 2:1, tend to discourage side reactions such as the decomposition of CO to form carbon (coke), but the yield of $C_2$ plus hydrocarbon products also decreases at the higher $H_2$ to CO ratios.

If the hydrogen to CO mole ratio is below about 2:1, a secondary water-gas shift reaction can occur as shown by Equation 2:

Equation 2

$$CO + H_2O \rightleftarrows CO_2 + H_2$$

Methane and $CO_2$ may also be produced as shown in Equation 3:

Equation 3

$$2CO + 2H_2 \rightleftarrows CH_4 + CO_2$$

If $CO_2$ is present either initially or via Equations 2 and 3, methane and $C_2$ and higher hydrocarbons can also be produced as shown in Equation 4:

Equation 4

$$(3n + 1)H_2 + nCO_2 \rightleftarrows C_nH_{2n+2} + 2nH_2O$$

For instance, when $n$ equals one,

Equation 4(a)

$$4H_2 + CO_2 \rightleftarrows CH_4 + 2H_2O$$

and when $n$ equals three,

Equation 4(b)

$$10 H_2 + 3CO_2 \rightleftarrows C_3H_8 + 6H_2O$$

Since hydrogen is the more expensive component of the charge stock, it is naturally preferred to keep the $CO_2$ content of the charge stock as low as possible, albeit a charge consisting essentially of $CO_2$ can be employed if desired. The higher molar ratios of $H_2$ to carbon oxides, as noted previously, can be used to a limit of 4:1 despite the relative high cost of hydrogen.

The charge stock for the reaction of synthesis gas of this invention can, of course, be obtained from any suitable source well known to those in the art. For example, if pipeline gas (SNG and LPG, i.e. methane and $C_2$–$C_6$ hydrocarbons, respectively) is the desired final product, the charge stock for the synthesis reaction can be derived from the gasification of coal with steam and oxygen. Initial coal gasification product streams are too low in hydrogen and contain undesirable impurities, especially sulfur compounds which tend to deactivate the catalysts of this invention. A typical coal gasification product on a water-free basis contains about 29% $CO_2$; 19% CO; 38% $H_2$; 13% methane; and small amounts of $H_2S$ and nitrogen. Normally these gases are purified to remove sulfur (to less than 1 ppm), and the gases are then subjected to a water-gas shift reaction (Equation 2) to increase the $H_2$ and thus give a product gas stream which is suitable as a charge stock to a synthesis reactor, e.g. where the $H_2$ to combined carbon oxides is from 1:1 to 4:1.

Diluent gases such as nitrogen or steam can also be present in the charge stock and the amount of inert material in the charge must be balanced by its usefulness as a heat sink versus the reduced space-time yields of products which are achieved because of the presence of the diluent. In one preferred embodiment of the invention, recycle product (after removal of LPG) consisting primarily of methane is used as the diluent heat sink.

The synthesis reaction occurs by contacting the charge stock with the desired catalyst under synthesis conditions including a temperature from 300° to 500° F. (149° to 260° C.), preferably from 350° to 450° F. (177° to 232° C.), and most preferably from 375° to 425° F. (190° to 218° C.). It is also desirable to utilize an adiabatic reactor such as are commonly employed in Fischer-Tropsch or methanol synthesis. The reaction is highly exothermic and, as noted previously, it is preferred to recycle a portion of the LPG-free product to serve as a heat sink.

The charge stock is usually preheated to a temperature of 300° to 450° F. (149° to 232° C.). This preheated gas is then contacted with the rare earth promoted metal chrysotile catalyst of this invention under synthesis conditions. By "under synthesis conditions" is meant under conditions of temperature, pressure and space velocity for the charge stock whereby the desired hydrocarbon products are produced by the reaction of $H_2$ and CO and/or $CO_2$. Such synthesis conditions, except for temperature, are not critical and are well known to those in this art. The temperature of the reaction, as noted, can be at least 300° F. (149° C.), preferably at least 350° F. (177° C.) and can be as high as 500° F. (260° C.) but, is preferably not above 450° F. (232° C.). The gaseous hourly space velocity (GHSV) can suitably be from 1 to 100,000 volumes of gas (total gas including recycle product) per volume of reactor per hour, preferably 100 to 10,000 v/v/hr, and most preferably 200 to 2000 v/v/hr. The reaction pressure is normally atmospheric to 1000 psi; however, increased pressures of up to 10,000 psi or more can be employed. An upflow fixed bed operation using extrudates, pellets or other suitably shaped and sized catalyst particles can be employed, but obviously, downflow operation or other types of catalyst beds, e.g. fluid beds, can also be employed.

The product from the reactor differs in composition from the charge stock by an increase in the concentration of methane, higher hydrocarbons and water, and a decrease in the content of hydrogen and carbon oxides. A portion of the product, usually free of LPG, is suitably recycled for admixture with the preheated charge stock to serve as a heat sink in the reactor. The recycle to feed gas volume ratio is usually about 2:1 but can be from 5:1 to 10:1 or more as desired.

The invention will be further described with reference to the following experimental work.

EXPERIMENTAL WORK

Example 1
(Preparation of Synthetic Nickel Chrysotile)

A synthetic nickel chrysotile was prepared by adding 35 g. Ludox S.A. (DuPont brand name) colloidal silica with stirring to a solution consisting of 60.1 g. of $NiCl_3.6H_2O$ dissolved in 105 cc. of water. pH electrodes were then immersed in the solution and an initial pH recording was made. A solution of 30 g. NaOH in 70 cc. of water was then added to the $NiCl_3.6H_2O$-colloidal silica mixture with stirring, until a final pH of 12 was obtained. The final mixture was stirred for an additional 10 minutes and placed into an autoclave where it was heated under autogenic pressure for 24 hours at 500° F. (260° C.).

After cooling, the resulting product, a slurry, was removed from the autoclave, filtered and washed with distilled water until free of NaCl. The precipitate was dried at 250° F. (121° C.) overnight. An X-ray diffraction pattern of the product corresponded to the crystalline compound of the formula $Ni_3(OH)_4.Si_2O_5$ (nickel chrysotile). The amount of nickel in the nickel chrysotile was 46.31 weight percent. The X-ray diffraction pattern is shown on Table 1.

TABLE 1

| X-RAY POWDER DIFFRACTION PATTERN | |
|---|---|
| d (A) | I |
| 7.50 | s |
| 4.50 | m |
| 3.67 | s |
| 2.58 | m |
| 2.46 | m |
| 2.10 | w |
| 1.725 | 2 |
| 1.545 | m |

TABLE 1-continued

| X-RAY POWDER DIFFRACTION PATTERN | |
|---|---|
| d (A) | I |
| 1.320 | w |
| 1.300 | w |

The sample was submitted for a surface area measurement by the BET method, and the material was found to have a surface area of approximately 150 $m^2/g$.

The preparation of nickel chrysotile followed the procedure of examples 1 through 11 in the Robson U.S. Pat. No. 3,729,429 except $NiCl_2$ was used in lieu of $MgCl_2$.

EXAMPLE 2
(Impregnation of Nickel Chrysotile with Thoria)

The wet filtrate in Example 1 was dried at 250° F. (121° C.) for 6 hours, and 100 grams of the dried filtrate were impregnated with 60 cc of a 5.22 weight percent aqueous solution of $Th(NO_3)_4.4H_2O$ by the so-called incipient wetness technique. The catalyst was dried at 250° F. (121° C.) for 6 hours and calcined in air at 350° F. (177° C.) for 12 hours. The weight percent of thoria in the nickel chrysotile catalyst was 1.5 by analysis.

A first series of experiments was performed using various catalysts to determine in detail the composition of the $C_2+$ hydrocarbon fraction. The products which resulted from using four different rare earth containing nickel chrysotile catalysts were separately analyzed by gas chromatography.

For the first series of experiments, the catalysts were loaded separately into a quartz reactor, and a gas consisting of pure carbon monoxide and hydrogen wherein the molar ratio of hydrogen to carbon monoxide was equal to 2.5 was passed through the catalyst bed at a space velocity of 350 GHSV and a temperature of 400° F. (204° C.) at atmospheric pressure. The results of these runs are listed in Table 2.

Referring to Table 2, it can be seen that the rare earth metal promoted catalysts of this invention are very selective for the formation of $C_2$ to $C_6$ hydrocarbons and especially $C_3$-$C_5$ hydrocarbons. As can be seen from the data in Examples 3 through 5, the percentage of hydrocarbons in the $C_2$ to $C_6$ range for the rare earth promoted catalysts are from 69.4 (Ex. 3) to 95 (Ex. 5), and as high as 96.5 (Ex. 4) for mixed rare earths. In Examples 3-5, the mole percent $C_3$-$C_5$ in the methane-free hydrocarbon product exceeded 50. Example 6, which employs manganese in addition to $La_2O_3$ as a promoter, shows only a selectivity of 26.8% to the production of products in the $C_2$ to $C_6$ range and a much higher percentage of $C_9$ and higher products.

TABLE 2

| Composition of Hydrocarbon Product | | | | |
|---|---|---|---|---|
| | Mole % Using | | | |
| Ex. No. | 3 | 4 | 5 | 6 |
| Catalyst-<br>Ni Chrysotile plus: | 2 wt %<br>$ThO_2$[1] | 2 + 2 wt %<br>$ThO_2$[2]<br>and $LaO_2$ | 2 wt %<br>$La_2O_3$[3] | 5 wt %<br>$MnO_2$[4]<br>+<br>2% $La_2O_3$ |
| Wt % Conversion of CO: | 30 | 68 | 26 | 24 |
| Mol % $CH_4$ in Hydrocarbon product | 58 | 52 | 66 | 66 |
| in Hydrocarbon product | 42 | 48 | 34 | 45 |
| Breakdown of $C_2$ + hydrocarbons in the methane-free hydrocarbon product | | | | |
| Mol % $C_2$-$C_6$ Hydrocarbons | 69.4 | 96.50 | 95.0 | 26.8 |
| Mol % $C_3$-$C_5$ Hydrocarbons | 54.4 | 82.7 | 55.0 | 14.8 |

TABLE 2-continued

| | Composition of Hydrocarbon Product | | | |
|---|---|---|---|---|
| | Mole % Using | | | |
| Ex. No. | 3 | 4 | 5 | 6 |
| Mol % $C_7$ + Hydrocarbons | 30.6 | 3.4 | 5.0 | 72.2 |
| Composition of methane-free hydrocarbon products (Mol %) | | | | |
| Carbon No. | | | | |
| 2 | 4.5 | 6.8 | 35.0 | 1.2 |
| 3 | 20.0 | 41.4 | 27.5 | 2.7 |
| 4 | 19.1 | 22.9 | 17.5 | 5.4 |
| 5 | 15.3 | 18.4 | 10.0 | 6.7 |
| 6 | 10.5 | 7.0 | 5.0 | 10.8 |
| 7 | 8.2 | 2.0 | 2.5 | 16.3 |
| 8 | 7.4 | 1.4 | 2.5 | 22.0 |
| 9 | — | — | — | 17.6 |
| 10 | — | — | — | 8.2 |
| 11 | — | — | — | 5.4 |
| 12 | — | — | — | 2.7 |
| % $C_9$ and higher | 15% | 0% | 0% | 33.9% |
| % $C_{13}$ and higher | — | — | — | 1.0% |

[1] Same as catalyst of Ex. 2 except enough thorium nitrate was used to produce 2% thoria on the final catalyst.
[2] Same as catalyst used in Ex. 3 except lanthanum nitrate added to deposit 2% $LaO_2$ on final catalyst.
[3] Same as catalyst used in Ex. 3 except La used in place of Th.
[4] Prepared as in Ex. 5 except sufficient manganese nitrate was used to deposit 5 wt % $MnO_2$.

The prior art teaches that manganese is an effective promoter for nickel catalysts for the production of gasoline range hydrocarbons as noted above on page 2. The addition of manganese to the nickel chrysotile functions as expected in that about 75% of the methane-free hydrocarbon product is above $C_6$, even though the nickel chrysotile also is promoted with a rare earth metal ($La_2O_3$). As also noted on page 2, the addition of thoria to certain prior art nickel catalysts is known to promote the production of gasoline range hydrocarbons. Quite surprisingly and in accordance with the invention, the addition of a rare earth metal such as thoria to a specific nickel catalyst, i.e. nickel chrysotile, results in the production of 60 mole percent or more, usually 70 to 90 mole percent or more, of low molecular weight hydrocarbons having two to six carbon atoms per molecule in the methane-free hydrocarbon product. In other words, it has been discovered that the product distribution can be surprisingly affected by the type of nickel catalyst which is promoted with the rare earth metal. There is in fact a peaking of $C_2$-$C_6$ paraffins in the hydrocarbon product with a corresponding decrease in the $C_7$+ products using the catalyst of this invention.

The process of this invention optimizes or peaks the production of LPG type hydrocarbon product as contrasted with the Fischer-Tropsch synthesis which produces gasoline and diesel range hydrocarbons in the $C_5$ to $C_{12}$ range and higher. This peaking or optimization is as shown by the data in Table 2 above, and the data to follow is a function of (i) the use of the specific nickel chrysotile catalyst promoted with a rare earth metal; (ii) the use of low temperatures in the range of 300° to 500° F. (149° to 260° C.); and (iii) the use of $H_2$ to CO mole ratios in the feed of from 1:1 to no more than 4:1.

A second series of runs was made to study the conversion of synthesis gas (3:1 $H_2$ to CO) at atmospheric pressure and a gaseous hourly space velocity of 300 volumes of synthesis gas per volume of catalyst per hour (GHSV) using either (1) nickel chrysotile or (2) 1.5 weight percent thoria promoted nickel chrysotile. The results are shown in Table 3.

TABLE 3

| Reaction Conditions | | Products Composition Mole % | | | | | | |
|---|---|---|---|---|---|---|---|---|
| | | Catalyst: Nickel Chrysotile | | | | Catalyst: 1.5% Thorium - Nickel Chrysotile | | |
| Temp. °F. | (°C.) | Ex. No. | CO | $CH_4$ | $C_{2+}$ | Ex. No. | CO | $CH_4$ | $C_{2+}$ |
| 250 | (121) | 7 | 100 | 0 | 0 | — | — | — | — |
| 300 | (149) | 8 | 99.1 | 0.1 | 0 | 16 | 94.0 | 5.5 | 0.5 |
| 350 | (177) | 9 | 99.5 | 0.5 | 0 | 17 | 85.4 | 12.2 | 2.4 |
| 375 | (191) | 10 | 98.0 | 2.0 | 0 | 18 | 68.2 | 19.3 | 12.5 |
| 400* | (204) | 11 | 83.0 | 17.0 | 0 | 19 | 41.0* | 41.2* | 17.8* |
| 400 | (204) | 12 | — | — | — | 20 | 38.7 | 41.2 | 20.1 |
| 450 | (232) | 13 | 30.3 | 69.7 | 0 | 21 | 13.0 | 76.2 | 10.8 |
| 500 | (260) | 14 | 1.2 | 98.9 | 0 | 22 | 0.2 | 93.8 | 6.0 |
| 600 | (316) | 15 | 0.5 | 99.5 | 0 | 23 | 0 | 99.0 | 1.0 |

*With addition of 5% of water into the feed gas

Referring to Table 3, Examples 7 through 15 show that synthesis gas reactin over nickel chrysotile results only in the production of methane, and little reaction is noted at temperatures below about 400° F., (204° C.). The addition of thoria increases the activity of the catalyst as noted by a comparison of Examples 10 and 18 where at 375° F. (191° C.) only 2% of the CO was reacted with the nickel chrysotile, whereas 32% of the CO was reacted with the thoria promoted catalyst. Additionally, the thoria greatly influences the selectivity of the nickel chrysotile. This is shown by a comparison of Examples 16 through 23 with Examples 7 through 15. In Examples 16 through 23, varying amounts of $C_2$+ products were noted, whereas no such products were observed using the unpromoted nickel chrysotile catalyst. However, at temperatures of 600° F. (316° C.), mostly methane was produced, even with the promoted catalyst. Thus, the process of this invention is operated at temperatures of 300° to 500° F. (149° to 260° C.), preferably 350° to 450° F. (149° to 232° C.).

The catalyst of Example 2 (thoria promoted nickel chrysotile) was used in a third series of runs to study the effect of the hydrogen to carbon monoxide ratio on the product composition. The procedure was the same as noted for the second series of runs except the temperature was 395° F. (201° C.). The results of the second series of runs are shown in Table 4.

TABLE 4
Effect of $H_2$:CO Ratio on Product Composition Using Thoria-Nickel Chrysotile Catalyst

| Ex. No. | $H_2$:CO | CO Conversion % | Mole % Selectivity to $CH_4$ | $C_{2+}$ |
|---|---|---|---|---|
| 24 | 4 | 43.5 | 85.2 | 14.8 |
| 25 | 3 | 38.7 | 67.2 | 33.8 |
| 26 | 2.5 | 29.0 | 55.0 | 45.0 |
| 27 | 2.2 | 19.0 | 51.5 | 48.5 |
| 28 | 2.0 | 14.0 | 43.2 | 56.8 |
| 29 | 1.8 | 8.0 | 40.8 | 59.2 |

By "selectivity" in this application is meant the moles of $CH_4$ or $C_{2+}$ products times 100, divided by the total moles of $CH_4$ plus $C_{2+}$ products.

Referring to Table 4, it is noted that the selectivity of the rare earth promoted catalyst for $C_{2+}$ hydrocarbons increases as the hydrogen to carbon monoxide ratio decreases. When the hydrogen to carbon monoxide ratio is 2.2 (Ex. 23), the product composition using the thoria nickel chrysotile catalyst is approximately 50% $CH_4$ and 50% $C_{2+}$ hydrocarbons. Preferably the process of this invention is operated at an $H_2$ to CO ratio of 1:1 to 2.5:1; more preferably 1:1 to 2.2:1.

A similar series of experiments was run using pure nickel chrysotile. Varying the hydrogen to carbon monoxide ratio did not alter significantly the product composition consisting mostly of methane.

A fourth series of runs was made to study the effect of thoria concentration of the nickel chrysotile on the composition of the products achieved by the reaction of synthesis gas under the following reaction conditions: 2.5 hydrogen to carbon monoxide ratio, 410° F. (210° C.); atmospheric pressure; and 350 GHSV. The results of these runs are shown in Table 5.

TABLE 5
Effect of Thoria Concentration on Product Composition

| Ex. No. | Wt % $ThO_2$ | % CO Conversion | Mol % Selectivity to $CH_4$ | $C_{2+}$ |
|---|---|---|---|---|
| 30 | 0.5 | 31.1 | 92.0 | 8.0 |
| 31 | 1.5 | 29.0 | 55.0 | 45.0 |
| 32 | 2.0 | 30.5 | 57.0 | 43.0 |
| 33 | 3.0 | 33.2 | 57.5 | 42.5 |
| 34 | 5.0 | 31.0 | 54.3 | 45.7 |
| 35 | 10.0 | 28.6 | 55.5 | 44.5 |
| 36 | 20.0 | 21.4 | 58.2 | 41.8 |
| 37 | 30.0 | 11.2 | 50.3 | 49.7 |

Referring to Table 5 it is demonstrated that increasing the weight percent of rare earth in the nickel chrysotile catalyst has little effect on the selectivity of the products (Exs. 31 through 37). In addition, comparing Example 37 in Table 5 with Example 11 in Table 3 shows that 30 weight percent $ThO_2$ on the catalyst does not appear to promote the activation of the nickel chrysotile catalyst.

A fifth series of experiments was made to determine the effect of the rare earth promoted nickel chrysotile catalyst composition on product selectivity. The rare earth nickel chrysotile catalysts used in Examples 38 through 43 on Table 6 below were prepared according to the preparation in Example 2, except instead of impregnating with an aqueous solution of thorium nitrate which gave a 1.5 weight percent of thoria in nickel chrysotile, aqueous rare earth nitrate solutions which gave 2 weight percent thoria, 2 weight percent lanthanum, 2.5 weight percent cerium, 2 weight percent praesodymium, 2+2 weight percent thoria plus lanthanum, and 2+2 weight percent thoria plus praesodymium, respectively, were used. The results are shown in Table 6 below.

In all of the examples in Table 6, the catalysts were loaded separately into a quartz reactor; and a gas consisting of pure carbon monoxide and hydrogen wherein the molar ratio of hydrogen to carbon monoxide was equal to 2.3 was passed through the catalyst bed at a space velocity of 400 GHSV and a temperature of 400° F. (204° C.) at atmospheric pressure.

TABLE 6
Relation of Catalyst Composition to Conversion and Product Selectivity

| Ex. No. | Catalyst | Wt % Rare Earth | % CO Conversion | % Selectivity to $C_{2+}$ |
|---|---|---|---|---|
| 11 | Ni-Chrysotile | 0 | 17.0 | 0 |
| 38 | Th-Ni Chrysotile | 2 | 31.5 | 43.0 |
| 39 | La-Ni Chrysotile | 2 | 25.0 | 39.0 |
| 40 | Ce-Ni Chrysotile | 2.5 | 32.5 | 32.1 |
| 41 | Pr-Ni Chrysotile | 2 | 35.3 | 35.0 |
| 42 | Th+La-Ni Chrysotile | 2+2 | 71.5 | 49.0 |
| 43 | Th+Pr-Ni Chrysotile | 2+2 | 69.1 | 48.0 |

Keeping in mind the data in Table 5 that the weight percent of the rare earth in the catalyst has little effect on the selectivity of products, and referring to Table 6, surprising and unexpected results are observed. Thoria doped nickel chrysotile gives 31.5% CO conversion, and lanthanum doped nickel chrysotile gives 25.0% CO conversion. By incorporating both thoria and lanthanum rare earths on nickel chrysotile, the expected result would be intermediate conversion between the result of using thoria alone and the result of using lanthanum alone. But surprisingly, the percent CO conversion using a thoria-lanthanum nickel chrysotile results in a 71.5% CO conversion which is an increase over using either thoria or lanthanum alone. Likewise, the same result occurred when thoria and praesodymium were employed (Ex. 43). In addition, when mixed rare earth-containing nickel chrysotile catalysts were used, the percent selectivity to $C_{2+}$ hydrocarbons also increased.

Resort may be had to such variations and modifications as fall within the spirit of the invention and the scope of the appended claims.

We claim:

1. A process which comprises contacting a charge stock comprising hydrogen and at least one carbon oxide selected from the group consisting of CO and $CO_2$ wherein the molar ratio of hydrogen to combined carbon oxide is from 1:1 to 4:1 under reaction conditions including a temperature of from 300° F. to 500° F. with a catalyst consisting essentially of a rare earth promoted metal silicate characterized as having repeating units of the structural formula:

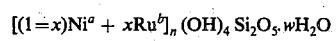

$$[(1-x)Ni^a + xRu^b]_n (OH)_4 Si_2O_5 \cdot wH_2O$$

where $x$ is a number from 0 to 1, this number expressing the atomic fraction of the metals nickel and ruthenium; $a$ is the valence of nickel; $b$ is the valence of ruthenium; $n$ is a number equal in value to that defined by the ratio $6/[a(1=x) + bx]$ and w is a number ranging from 0 to 4;

and thereafter recovering a product, which product, on a methane-free hydrocarbon basis contains at least 60 mole percent of low molecular weight hydrocarbons having from 2 to 6 carbon atoms per molecule.

2. A process according to claim 1 wherein the metal silicate is nickel chrysotile.

3. A process according to claim 2 wherein the amount of rare earth metal is from 0.5 to 25 weight percent of the final catalyst.

4. A process according to claim 3 wherein the rare earth metal is thorium.

5. A process according to claim 3 wherein the rare earth metal is lanthanum.

6. A process according to claim 3 wherein the rare earth metal is cerium.

7. A process according to claim 3 wherein the rare earth metal is praesodymium.

8. A process according to claim 3 wherein the rare earth metal is a mixture of rare earth metals.

9. A process according to claim 8 wherein the mixture of rare earth metals is thorium and lanthanum.

10. A process according to claim 8 wherein the mixture of rare earth metals is thorium and praesodymium.

11. A process according to claim 3 wherein the rare earth metal is added to the nickel chrysotile by deposition.

12. A process according to claim 11 wherein the rare earth metal is deposited from an aqueous solution of a rare earth metal nitrate.

13. A process according to claim 12 wherein the rare earth metal nitrate is thorium nitrate.

14. A process according to claim 12 wherein the rare earth metal nitrate is praesodymium nitrate.

15. A process according to claim 3 wherein the rare earth metal is incorporated into the catalyst during the preparation of the nickel chrysotile.

16. A process according to claim 15 wherein the nickel chrysotile is a synthetic nickel chrysotile prepared by combining a hydrous silicate solution with a metal oxide or hydroxide solution containing a rare earth salt in an alkaline medium at a pH above 10; and thereafter calcining.

17. A process according to claim 16 wherein the rare earth salt is thorium nitrate.

18. A process according to claim 16 wherein the rare earth salt is lanthanum nitrate.

19. A process according to claim 16 wherein the rare earth salt is cerium nitrate.

20. A process according to claim 16 wherein the rare earth salt is praesodymium nitrate.

21. A process according to claim 16 wherein the rare earth metal salt is a mixture of rare earth metal salts.

22. A process according to claim 21 wherein the rare earth metal salt mixture is comprised of thorium nitrate and lanthanum nitrate.

23. A process according to claim 21 wherein the rare earth metal salt mixture is comprised of thorium nitrate and praesodymium nitrate.

24. A process according to claim 16 wherein the pH is 12 to 14.

25. A process according to claim 2 wherein the methane-free hydrocarbon product contains at least 70 mole percent of paraffins having 2 to 6 carbon atoms per molecule.

26. A process according to claim 2 wherein the methane-free hydrocarbon product contains at least 90 mole percent of paraffins having from 2 to 6 carbon atoms per molecule.

27. A process which comprises contacting a charge stock comprising hydrogen and at least one carbon oxide selected from the group consisting of CO and $CO_2$ wherein the molar ratio of hydrogen to combined carbon oxide is from 1.5:1 to 2.5:1 under reaction conditions including a temperature of from 350° F. to 450° F. with a catalyst consisting essentially of a rare earth metal promoted metal silicate characterized as having repeating units of the structural formula:

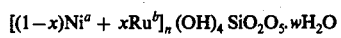

where x is a number from 0 to 1, this number expressing the atomic fraction of the metals nickel and ruthenium; a is the valence of nickel; b is the valence of ruthenium; n is a number equal in value to that defined by the ratio $6/[a(1-x) + bx]$ and w is a number ranging from 0 to 4;

and thereafter recovering a hydrocarbon product consisting of at least about 50 weight percent on a methane free basis of paraffins having at least two carbon atoms per molecule and where in said hydrocarbon product the hydrocarbon distribution is such that at least 60 mole percent of said hydrocarbon product has from 2 to 6 carbon atoms per molecule.

28. A process according to claim 27 wherein the rare earth metal is thorium and the amount of rare earth metal is from 0.5 to 10 weight percent of the final catalyst.

29. A process according to claim 27 wherein said rare earth metal is a mixture of rare earth metals and the amount of said rare earth metals is from 0.5 to 10 weight percent of the final catalyst.

30. A process according to claim 27 wherein the metal silicate is nickel chrysotile; the hydrogen to combined carbon oxide ratio is from 1.5:1 to about 2:1; the reaction temperature is from 375° F. to 425° F.

31. A process according to claim 30 wherein the rare earth metal is thorium and the amount of rare earth metal is from 0.5 to 10. weight percent of the final catalyst.

32. A process according to claim 30 wherein said rare earth metal is a mixture of rare earth metals and the amount of said rare earth metals is from 0.5 to 10 weight percent of the final catalyst.

33. A process according to claim 27 wherein the hydrocarbon distribution in said hydrocarbon product is such that more than 50% of said product has from 3 to 5 carbon atoms per molecule.

* * * * *

UNITED STATES PATENT OFFICE
CERTIFICATE OF CORRECTION

Patent No. 4,116,995  Dated September 26, 1978

Inventor(s) Thaddeus P. Kobylinski and Harold E. Swift

It is certified that error appears in the above-identified patent and that said Letters Patent are hereby corrected as shown below:

Abstract - line 8, in the formula, "$Ru^6$" should be --$Ru^{\bar{b}}$--;

Col. 5, line 22, that part of the formula which reads "$H2^O$" should read --$H_2O$--;

Col. 8, Table 2, under "Ex. No.", line 6, insert before "in Hydrocarbon" the following: --Mol % $C_2$+ Hydrocarbons--

Col. 10, Table 3, 5th column of Table, next to last line: "98.9" should be --98.8--.

Signed and Sealed this

Nineteenth Day of June 1979

[SEAL]

Attest:

RUTH C. MASON
Attesting Officer

DONALD W. BANNER
Commissioner of Patents and Trademarks